(12) United States Patent
Ogle et al.

(10) Patent No.: US 10,849,684 B2
(45) Date of Patent: Dec. 1, 2020

(54) ELECTRICAL LEAD FOR A CATHETER AND METHOD OF MANUFACTURING

(71) Applicant: CathRx Ltd, Homebush Bay (AU)

(72) Inventors: David Ogle, Cowan (AU); Roman Greifeneder, Bexley (AU); Warrick Heald, Fairlight (AU)

(73) Assignee: CathRx Ltd, Homebush Bay (AU)

( * ) Notice: Subject to any disclaimer, the term of this patent is extended or adjusted under 35 U.S.C. 154(b) by 861 days.

(21) Appl. No.: 14/894,970

(22) PCT Filed: Jun. 6, 2014

(86) PCT No.: PCT/AU2014/000591
§ 371 (c)(1),
(2) Date: Nov. 30, 2015

(87) PCT Pub. No.: WO2014/194368
PCT Pub. Date: Dec. 11, 2014

(65) Prior Publication Data
US 2016/0113710 A1 Apr. 28, 2016

(30) Foreign Application Priority Data
Jun. 7, 2013 (AU) ................ 2013902061

(51) Int. Cl.
*A61B 18/14* (2006.01)
*A61M 25/00* (2006.01)
(Continued)

(52) U.S. Cl.
CPC .......... *A61B 18/1492* (2013.01); *A61B 18/00* (2013.01); *A61M 25/005* (2013.01);
(Continued)

(58) Field of Classification Search
CPC .......... A61B 18/1492; A61B 2218/002; A61B 2218/003; A61B 2017/00526; A61M 25/005; A61M 25/0012
See application file for complete search history.

(56) References Cited

U.S. PATENT DOCUMENTS 3,585,707 A 6/1971 Stevens
5,016,646 A 5/1991 Gotthardt et al.
(Continued)

FOREIGN PATENT DOCUMENTS

CN 101500635 A 8/2009
EP 1256326 A1 11/2002
(Continued)

OTHER PUBLICATIONS

Australian First Office Action for Australian Application No. 2014277623, dated Jan. 15, 2018, 7 pages.
(Continued)

*Primary Examiner* — Michael F Peffley
*Assistant Examiner* — Samantha M Good
(74) *Attorney, Agent, or Firm* — TraskBritt (57) ABSTRACT

An electrical lead for a catheter includes an elongate member of non-conductive material having a proximal end and a distal end and defining a lumen extending from the proximal end to the distal end. The elongate member further includes a tubular member of non-conductive material, a braid of conductive material applied over the tubular member, an intermediate layer of non-conductive material applied over the braid, a plurality of electrical conductors extending from the proximal end to the distal end laid on the intermediate layer, and an outer layer of non-conductive material applied over the electrical conductors to cover the conductors. At least one electrode is arranged on the outer surface of the elongate member in electrical communication with at least
(Continued)

one of the plurality of electrical conductors through the outer layer. The braid underlies the at least one electrode but is insulated from the at least one electrode by the intermediate non-conductive layer.

22 Claims, 5 Drawing Sheets (51) Int. Cl.
A61N 1/05 (2006.01)
A61B 18/00 (2006.01)
A61N 1/375 (2006.01)
A61N 1/04 (2006.01)
A61B 17/00 (2006.01)

(52) U.S. Cl.
CPC ....... *A61M 25/0012* (2013.01); *A61N 1/0488* (2013.01); *A61N 1/05* (2013.01); *A61N 1/3752* (2013.01); A61B 2017/00526 (2013.01); A61B 2018/00577 (2013.01); A61B 2218/002 (2013.01)

(56) References Cited

U.S. PATENT DOCUMENTS

| | | | |
|---|---|---|---|
| 5,417,208 A | 5/1995 | Winkler | |
| 5,836,946 A | 11/1998 | Diaz et al. | |
| D550,840 S | 9/2007 | Anderson et al. | |
| 7,347,857 B2 | 3/2008 | Anderson et al. | |
| 7,415,300 B2 | 8/2008 | Anderson et al. | |
| D579,562 S | 10/2008 | Anderson et al. | |
| D599,904 S | 9/2009 | Anderson | |
| 7,740,629 B2 | 6/2010 | Anderson et al. | |
| 7,871,410 B2 | 1/2011 | Booth et al. | |
| 7,967,817 B2 | 6/2011 | Anderson et al. | |
| 8,062,284 B2 | 11/2011 | Booth | |
| 8,064,978 B2 | 11/2011 | Anderson et al. | |
| 8,100,895 B2 | 1/2012 | Panos et al. | |
| 8,251,977 B2 | 8/2012 | Partlett | |
| 8,260,394 B2 | 9/2012 | Anderson et al. | |
| 8,286,338 B2 | 10/2012 | Anderson et al. | |
| 8,506,562 B2 | 8/2013 | Anderson et al. | |
| 8,641,697 B2 | 2/2014 | Partlett et al. | |
| 8,690,871 B2 | 4/2014 | Partlett et al. | |
| 8,977,333 B2 | 3/2015 | Anderson et al. | |
| 9,008,795 B2 | 4/2015 | Milijasevic et al. | |
| 9,055,952 B2 | 6/2015 | Ryan | |
| 9,084,869 B2 | 7/2015 | Anderson et al. | |
| 9,107,673 B2 | 8/2015 | Chong et al. | |
| 9,108,022 B2 | 8/2015 | Ogle | |
| 2005/0010194 A1* | 1/2005 | Zhou ................... | A61M 25/001 604/527 |
| 2007/0129717 A1 | 6/2007 | Brown et al. | |
| 2008/0033497 A1 | 2/2008 | Bulkes et al. | |
| 2008/0161794 A1 | 7/2008 | Wang et al. | |
| 2008/0319418 A1 | 12/2008 | Chong | |
| 2009/0209975 A1 | 8/2009 | Milijasevic et al. | |
| 2009/0306653 A1 | 12/2009 | Anderson | |
| 2010/0106155 A1 | 4/2010 | Anderson et al. | |
| 2010/0217257 A1 | 8/2010 | Howat et al. | |
| 2010/0256693 A1 | 10/2010 | McDonald et al. | |
| 2011/0218603 A1 | 9/2011 | Victorine et al. | |
| 2011/0276034 A1 | 11/2011 | Tomarelli et al. | |
| 2012/0029444 A1* | 2/2012 | Anderson ......... | A61M 25/0012 604/264 |
| 2012/0130461 A1* | 5/2012 | Olsen ................... | A61N 1/3718 607/116 |
| 2012/0310238 A1 | 12/2012 | Ogle et al. | |
| 2012/0330121 A1 | 12/2012 | Anderson et al. | |
| 2013/0006238 A1* | 1/2013 | Ditter ................. | A61B 18/1492 606/41 |
| 2013/0060236 A1 | 3/2013 | Ogle | |
| 2013/0060237 A1 | 3/2013 | Ogle | |
| 2013/0144209 A1 | 6/2013 | Ryan | |
| 2013/0144224 A1* | 6/2013 | Ryan ................... | A61B 5/0422 604/264 |
| 2013/0144253 A1 | 6/2013 | Ryan et al. | |
| 2013/0150808 A1 | 6/2013 | Ogle et al. | |
| 2013/0282007 A1 | 10/2013 | Chong et al. | |
| 2014/0031907 A1 | 1/2014 | Williams | |

FOREIGN PATENT DOCUMENTS

| | | |
|---|---|---|
| JP | 2012510831 A | 5/2012 |
| JP | 2013013726 A | 1/2013 |
| JP | 2013533067 A | 8/2013 |
| WO | 8304182 A1 | 12/1983 |
| WO | 9413358 A1 | 6/1994 |
| WO | 9856448 A1 | 12/1998 |
| WO | 2006012671 A1 | 2/2006 |

OTHER PUBLICATIONS

Australian Second Office Action for Australian Application No. 2014277623, dated Apr. 9, 2018, 4 pages.
Chinese First Office Action for Chinese Application No. 201480032160.2, dated May 31, 2017, 16 pages.
Chinese Second Office Action for Chinese Application No. 201480032160.2, dated Jan. 22, 2018, 17 pages.
Chinese Supplementary Search Report for Chinese Application No. 201480032160.2, dated Jan. 11, 2018, 2 pages.
Chinese Search Report for Chinese Application No. 201480032160.2, dated May 19, 2017, 2 pages.
European Search Report for European Application No. 14807710.0, dated Dec. 16, 2016, 7 pages.
International Search Report from PCT International Application No. PCT/AU2014/000591, dated Sep. 24, 2014, 4 pages.
International Written Opinion from PCT International Application No. PCT/AU2014/000591, dated Sep. 24, 2014, 12 pages.
Japanese Search Report for Japanese Application No. 2016525914, dated Mar. 9, 2017, 30 pages.
European Communication pursuant to Article 94(3) EPC for European Application No. 14807710, dated Aug. 2, 2018, 5 pages.

* cited by examiner

ELECTRICAL LEAD FOR A CATHETER AND METHOD OF MANUFACTURING

CROSS-REFERENCE TO RELATED APPLICATIONS

This application is a national phase entry under 35 U.S.C. § 371 of International Patent Application PCT/AU2014/000591, filed Jun. 6, 2014, designating the United States of America and published in English as International Patent Publication WO 2014/194368 A1 on Dec. 11, 2014, which claims the benefit under Article 8 of the Patent Cooperation Treaty and under 35 U.S.C. § 119(e) to Australian Patent Application Serial No. 2013902061, filed Jun. 7, 2013, the disclosure of each of which is hereby incorporated herein in its entirety by this reference.

TECHNICAL FIELD

This disclosure relates, generally, to an electrical lead for a catheter and a method of manufacturing an electrical lead.

BACKGROUND

Any discussion of the prior art throughout the specification should in no way be considered as an admission that such prior art is widely known or forms part of common general knowledge in the field.

Electrophysiology catheters are commonly used in medical practice to examine and treat the heart. They may be inserted into the cardiovascular system of the patient through small punctures in the skin. They may then extend through a vein into the heart where they sense the electrical activity of the heart. Some of the electrophysiology catheters may be able to treat the heart by ablating the appropriate areas of the heart in case of certain types of aberrant electrical activity. In the treatment of a biological site in a patient's body, it is often necessary to cool the site being treated. This is effected by an appropriately sterilized liquid being applied at the site.

BRIEF SUMMARY

It is an object of this disclosure to overcome or ameliorate at least one of the disadvantages of the prior art, or to provide a useful alternative.

In an aspect, there is provided a method of fabricating an electrical lead for a catheter, the method comprising providing an elongate member having a proximal end and a distal end, and defining a lumen extending from the proximal end to the distal end, the elongate member including a tubular member of non-conductive material, a braid of conductive material applied over the tubular member, an intermediate layer of non-conductive material applied over the braid, a plurality of electrical conductors extending from the proximal end to the distal end laid on the intermediate layer, and an outer layer of non-conductive material applied over the electrical conductors to cover the conductors. The method further includes accessing at least one of the plurality of electrical conductors and forming an electrode on an outer surface of the elongate member in electrical connection with the at least one of the electrical conductors, wherein the braid underlies the electrode.

In an embodiment, the method includes arranging the plurality of electrical conductors helically on the intermediate layer about the tubular member.

In an embodiment, the method includes inserting a tubular irrigation passage into the lumen of the elongate member. Preferably, the cross-sectional shape of the irrigation passage is a kidney shape.

In an embodiment, the method further includes deforming the cross-sectional shape of the irrigation passage at its distal end into a circular shape by inserting an irrigation passage adapter to the distal end of the irrigation passage such that the irrigation passage adapter abuts the distal end of the irrigation passage against an inner wall of the elongate member.

In an embodiment, the method includes forming an end electrode by accessing at least one of the plurality of electrical conductors proximal the distal end of the elongate member and covering the distal end of the elongate member with an end electrode to overlie the at least one electrical conductor accessed and to be in electrical connection with the conductor.

There is also provided an electrical lead for a catheter that includes an elongate member of non-conductive material having a proximal end and a distal end and defining a lumen extending from the proximal end to the distal end, the elongate member including a tubular member of non-conductive material, a braid of conductive material applied over the tubular member, an intermediate layer of non-conductive material applied over the braid, a plurality of electrical conductors extending from the proximal end to the distal end laid on the intermediate layer, and an outer layer of non-conductive material applied over the electrical conductors to cover the conductors. The electrical lead further includes at least one electrode on an outer surface of the elongate member in electrical communication with at least one of the plurality of electrical conductors through the outer layer, wherein the braid underlies the at least one electrode but is insulated from the at least one electrode by the intermediate non-conductive layer.

In an embodiment, the plurality of electrical conductors are arranged helically on the intermediate layer about the tubular member.

In an embodiment, a tubular irrigation passage is inserted into the lumen of the elongate member. The cross-sectional shape of the irrigation passage is preferably a kidney shape.

In an embodiment, there is an irrigation passage adapter inserted into a lumen of the irrigation passage at its distal end, the irrigation passage adapter deforming the cross-sectional shape of the distal end of the irrigation passage into a circular cross-sectional shape, the irrigation passage adapter further abutting the distal end of the irrigation passage and pressing its circumference tightly against an inner wall of the elongate member.

In an embodiment, the electrical lead further includes an end electrode covering the distal end of the elongate member, the end electrode being in electrical communication with at least one of the plurality of electrical conductors through the outer layer.

BRIEF DESCRIPTION OF THE DRAWINGS

Preferred embodiments of the disclosure will now be described, by way of example only, with reference to the accompanying drawings in which.

DETAILED DESCRIPTION

Figure 1:
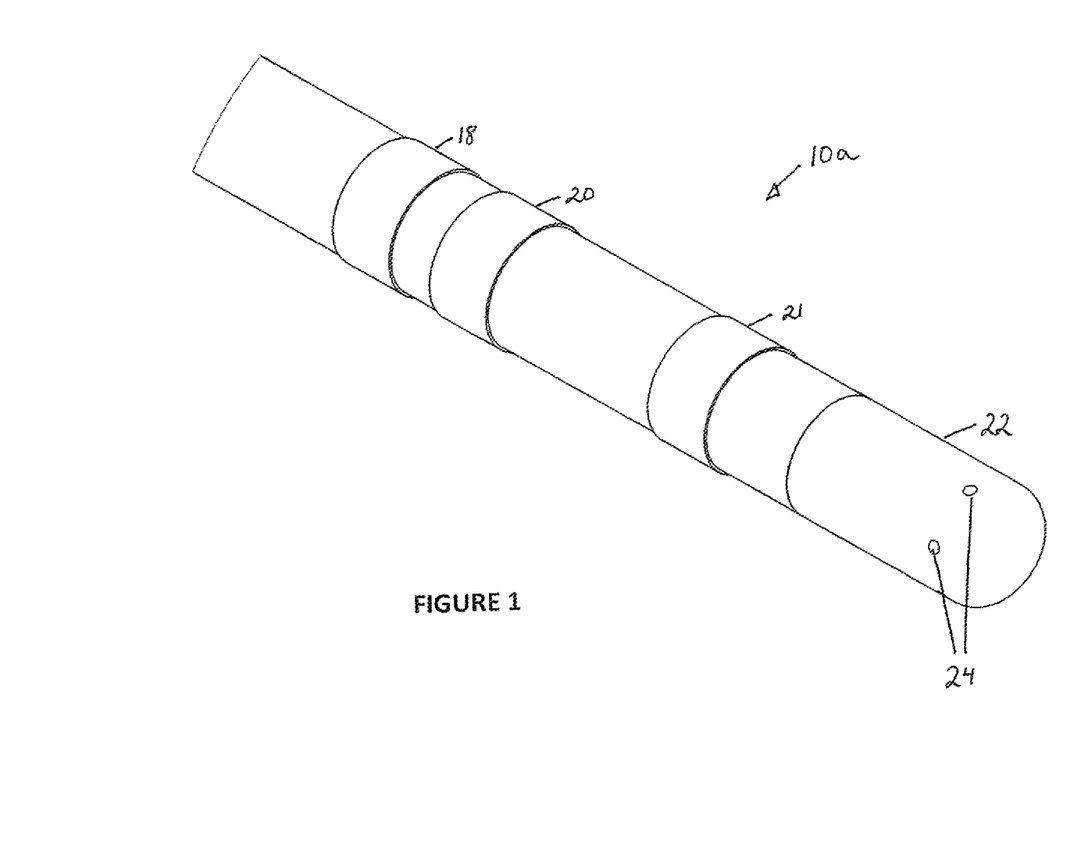
FIG. 1 shows a distal end of an ablation catheter.

In the drawings, reference numeral 10 generally designates an embodiment of an electrical lead made in accordance with a process for manufacturing an electrical lead as described below. The electrical lead 10 is suitable for use as a catheter sheath for an ablation catheter in which an ablating electrode 22 is cooled by supplying a cooling fluid for the ablating electrode. FIG. 1 depicts the distal end of such an ablation catheter. The catheter comprises an elongate electrical lead 10 having a proximal end 10b and a distal end 10a and defining a lumen extending from the proximal end 10b (shown in FIG. 2) to the distal end 10a. At least one sensing electrode 18, 20, 21 is arranged on the electrical lead 10 at the distal portion of the lead. In the ablation catheter of FIG. 1, the ablating electrode is the end electrode 22, which includes multiple openings 24 for the irrigation fluid.

Figure 2:
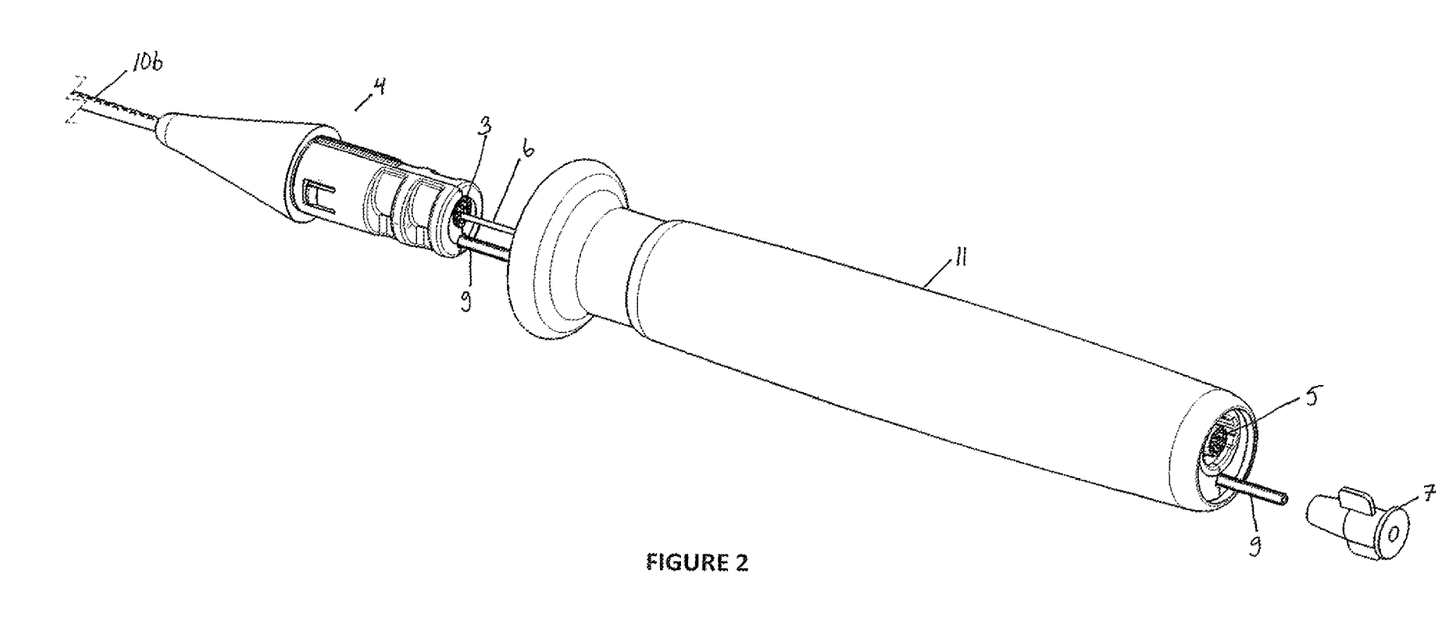
FIG. 2 shows a proximal part of an ablation catheter including a control handle.

The proximal part of the ablation catheter is shown in FIG. 2. The catheter includes a handle 11. The handle 11 is configured to receive a steering element 6 such as a stylet that can be used to deflect the distal end 10a of the catheter. Referring to FIG. 2, the electrical lead 10 removably connects to the handle 11 via a connector element 4. A steering element 6, such as a stylet, is received in the lumen of the electrical lead. The electrical lead connector element 4 includes an electrical connector 3 for connecting conductors from the electrical lead to a monitoring device via a second electrical connector 5 at the proximal end of the handle 11.

Terms "releasably connectable," "removably attached," and the like, as used herein, refers to arrangements whereby two components are configured in such a manner as to enable their connection/attachment, and enable that connection/attachment to be reversed without necessarily damaging either component. That is, the connection/attachment is repeatable. This is significant in the context of a modular device, as the various individual components may be interchanged between devices (for example, where some components are discarded after use, and others reprocessed (e.g., cleaned or otherwise serviced) for further use. It is also to be noted that each one of the steering element 6 and the electrical lead 10 may be fixedly attached to the handle. It is a preferred embodiment that the connection between the handle 11 and the steering element 6 or the electrical lead 10 is releasable.

In use, irrigation fluid is supplied to the fluid lumen of the catheter via the irrigation fluid connector element 7 and the irrigation passage 9. The irrigation passage 9 extends inside the handle and connects to a fluid connector element 7. The fluid connector element 7 is a luer connector or similar connector that ensures a sealing connection from the connector element 7 to the irrigation passage 9.

Figure 3:
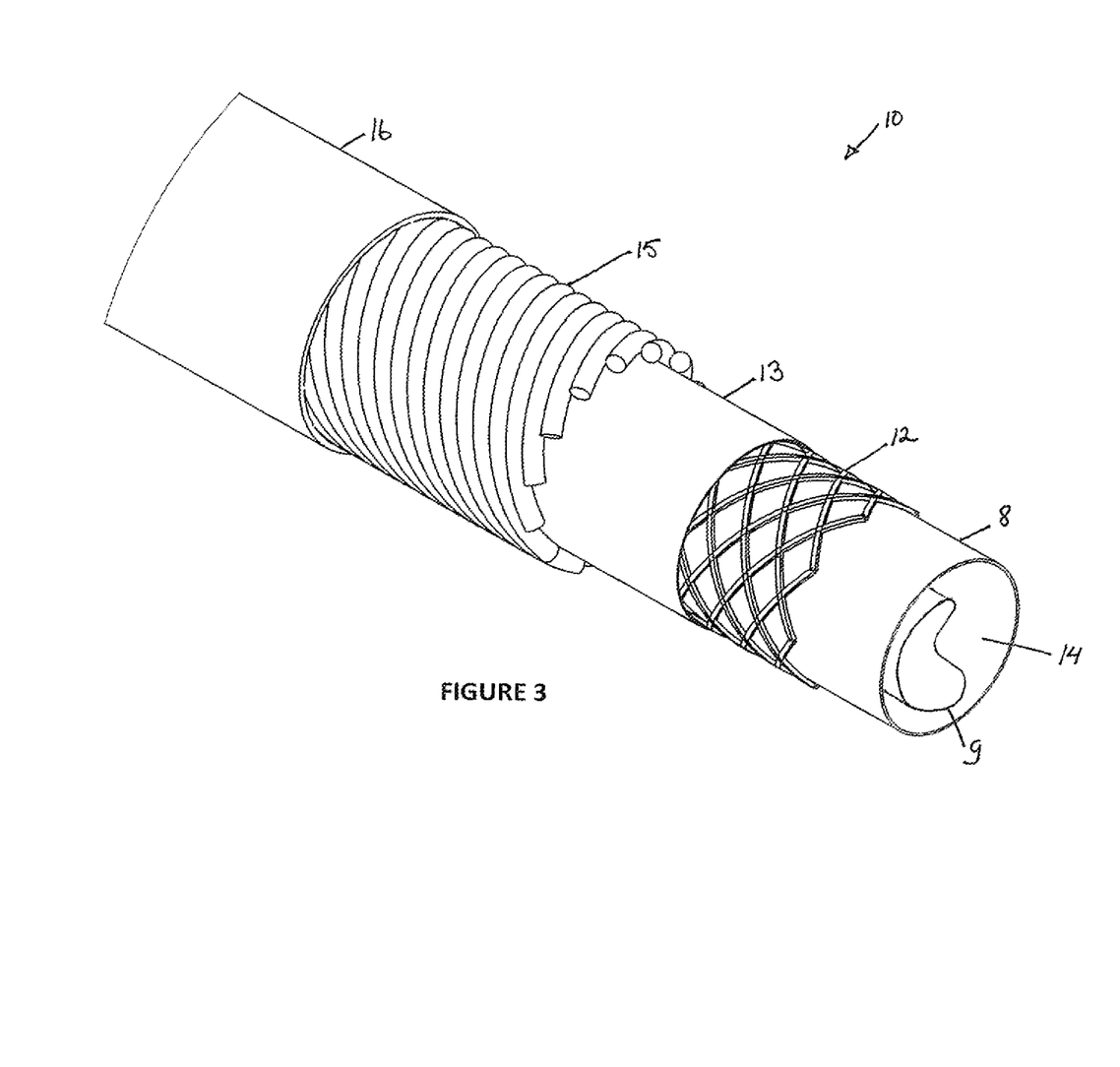
FIG. 3 shows a schematic view of the electrical lead.

Referring to FIG. 3, the electrical lead 10 has a first inner layer or member 8 of non-conductive material. The inner member 8 is tubular and it is formed by extruding a thin layer of the non-conductive material such as polytetrafluoroethylene (PTFE or TEFLON®) over a mandrel. The first inner layer 8 defines a lumen 14 for a steering element (not shown in FIG. 3) of the catheter and an irrigation passage 9 for the cooling fluid of the ablating electrode.

The first inner layer 8 provides a substrate for a reinforcing braid 12 to be applied to, along with facilitating a smooth pathway for both the irrigation passage 9 and the steering element 6 to be inserted into the lumen 14. The braid 12 is formed of stainless steel wire on the first inner layer 8. The braid 12 provides desirable rotational torque and bending stiffness characteristics to the electrical lead 10. The braid also provides sufficient flexibility to the electrical lead while preventing any kinking or other adverse bending of the lead.

The braid 12 is coated with a second non-conductive intermediate layer 13 of a suitable polymer, such as polyethylene or polyether block amide (PEBAX). A plurality of conductors 15 are coiled in a helical manner around the outer surface of the intermediate layer 13. The conductors 15 are metal wires that are insulated by a polymeric material such as nylon, polyurethane or a nylon-polyurethane co-polymer. The diameter of the conductor wires is such that the overall electrical resistance is as low as possible. Up to 24 conductors or more may be used, some of which are used for providing an electrical path for one or more sensing electrodes or one or more ablation electrodes and some are used as a thermocouple sensing the temperature of the one or more ablation electrodes. The intermediate layer 13 insulates the braid wire 12 from electrical short circuits and provides protection to the conductor wires' 15 insulation layer by preventing any cross-connection between the braid 12 and the conductors 15.

An outer polymeric sleeve 16 is formed, for example by extrusion, over the conductors to form the electrical lead 10. The third layer, being the outer polymeric sleeve 16, is made from materials similar to or the same as the second intermediate layer 13. The electrical lead 10 comprising the inner member 8, the braid 12, the intermediate layer 13, the conductors 15 and the outer polymeric sleeve 16 is heat treated to secure the outer polymeric sleeve 16 to the inner member 8, the braid 12, the intermediate layer 13 and to the conductors 15. Another method for applying the outer polymeric sleeve 16 over the conductors 15 is to apply molten outer polymeric material over the conductors 15 and allow it to set over time. It will be appreciated that a wall of the electrical lead 10 is, therefore, effectively made up of an inner layer defined by the inner member 8, the braid embedded in the intermediate layer 13, a layer made up of the helically wound conductors 15 and an outer layer defined by the outer polymeric sleeve 16. The conductors 15 are, in effect, embedded in the wall of the electrical lead and, as there is little, if any, polymeric material between adjacent turns of the conductors 15, there is the ability for limited movement between adjacent turns, thereby improving the flexibility of the electrical lead 10.

An irrigation passage 9 is an elongate fluid tube that is extruded from non-conductive material. The irrigation passage 9 is extruded over a mandrel to be a flexible, hollow tube having a cross-sectional area in the shape of a kidney. The kidney shape of the irrigation passage vacates enough space in the lumen 14 for the steering element to be inserted into the electrical lead (not shown in FIG. 3, 4, or 5).

One or more sensing electrodes 18, 20 and 21 are formed onto the electrical lead by laser cutting a portion of the outer polymeric sleeve 16 to expose a conductor lead and covering the exposed conductor by conductive material such as a platinum ring to form an electrode onto the electrical lead. Laser cutting is accurate and provides a suitable way of removing a portion of the outer polymeric sleeve 16 with ease to produce an opening. If the conductors 15 are insulated, the step of exposing the conductor(s) also cuts and removes the layer of insulation over the wires in addition to cutting and removing a corresponding portion of the outer polymeric sleeve 16.

The opening formed in the outer polymeric sleeve 16 is substantially filled with an electrically conductive paste or adhesive such as a silver-filled epoxy. The electrically conductive adhesive is then overlaid with a conductive biocompatible material, such as a platinum ring, that is affixed onto the outside of the electrical lead via a suitable process, such as dry swaging or crimping. Such electrodes 18, 20 and 21 have particular application as sensing electrodes.

The end ablating electrode 22 is formed in a similar manner to the sensing electrodes 18, 20 and 21. A conductor wire is exposed by laser, cutting close to the distal end of the electrical lead 10. The opening to the exposed conductor wire is then filled with conductive adhesive and an end electrode 22 is placed over the exposed conductor to seal the tip of the electrical lead 10. The conductor wire is used for transmission of ablation energy such as radio frequency (RF) energy to the end electrode.

Figure 4:
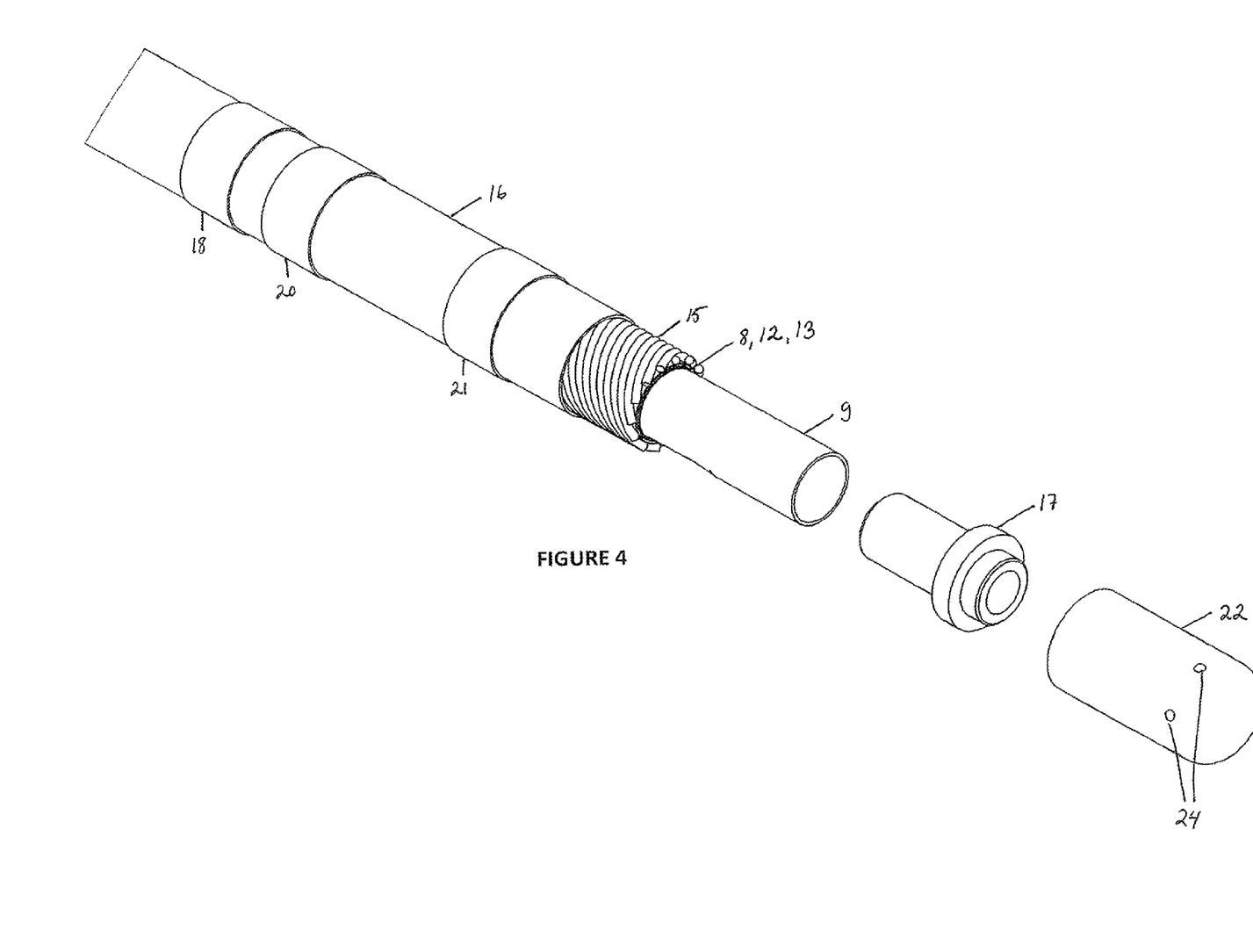
FIG. 4 shows an exploded view of a distal end of an ablation catheter.

The ablating end electrode 22 has a plurality of irrigation openings 24 formed in the body of the electrode. The benefit of this arrangement is that the irrigation fluid is expelled onto the surface of the ablation electrode and it cools the surrounding region of the electrode. Preferably, as shown in FIGS. 1 and 4 of the drawings, the ablating electrode has a plurality of such openings arranged at circumferentially spaced intervals. The process of forming the electrodes is described in more detail in International patent application No. PCT/AU2005/000834, which is incorporated herein by reference.

FIG. 4 shows an exposed view of the distal end 10a of the electrical lead 10. Although not individually shown in FIG. 4, the electrical lead 10 also includes the first inner member 8, the braid 12 and the intermediate layer 13. The advantage of having the tip electrode as an ablation electrode is that the braid can extend all the way to the distal tip electrode 22 of the electrical lead. Because of the helically wound conductor wires, the braid 12 can also extend under the sensing electrodes 18, 20, 21 providing beneficial torque and stiffness characteristics to the tip of the electrical lead 10 and to sensing electrodes 18, 20 and 21.

Figure 5:
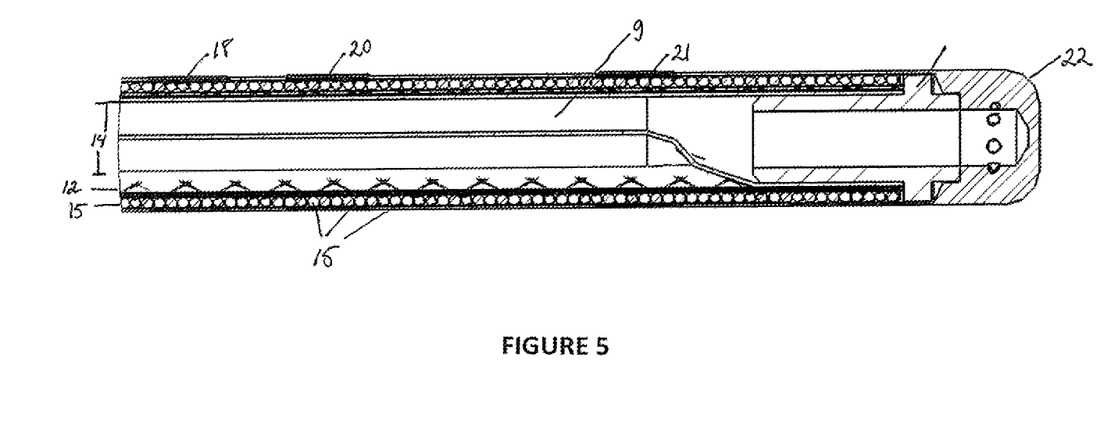
FIG. 5 shows a cross-sectional side view of a distal end of an electrical lead.

Referring to FIGS. 4 and 5, the kidney-shaped irrigation passage 9 is sealingly connected to the tip of the ablation electrode 22 via an irrigation passage adapter 17. The irrigation passage adapter 17 deforms the kidney-shaped distal end of the irrigation passage 9 into a circular shape so as to sealingly connect the irrigation passage 9 to the ablation electrode 22. As described above, the tip electrode 22 is affixed to the distal tip of the electrical lead by exposing one of the conductor wires 15 and attaching the tip electrode 22 over the exposed wire so as to be in electrical connection with the exposed conductor wire. The ablation electrode is then placed over the adapter 17 to cover and close the open distal end of the electrical lead. An appropriate sealing aid, such as an adhesive, may be used to secure the irrigation passage adapter 17 and/or the ablation electrode 22 in place so that the only path for the irrigation fluid is sealed from the irrigation fluid connector element 7 at the proximal end of the catheter handle through the irrigation passage 9 and the irrigation openings 24.

It is an advantage of the described embodiments that this disclosed manufacturing technique for an electrical lead of an ablation catheter lends itself to the use of non-conductive elongate elements to be positioned in the lumen 14 of the electrical lead 10. Thus, an irrigation passage 9 can be formed in a cost-effective way. Advantageously, an ablation catheter is able to be provided that is of a substantially smaller diameter than other catheter sheaths of which the Applicant is aware. Due to the manufacturing techniques employed, the electrical lead 10 need be no wider than a conventional non-ablation catheter. This is beneficial for the ease with which the clinician can steer the catheter through a patient's vasculature as the catheter is steered through the patient's body. Furthermore, the braid being able to extend to the tip of electrode 22 ensures reinforcement for improved pushability and torque transfer to the whole length of the catheter without compromising the thickness of the electrode lead.

Reference throughout this specification to "one embodiment," "some embodiments" or "an embodiment" means that a particular feature, structure or characteristic described in connection with the embodiment is included in at least one embodiment of the present invention. Thus, appearances of the phrases "in one embodiment," "in some embodiments" or "in an embodiment" in various places throughout this specification are not necessarily all referring to the same embodiment, but may. Furthermore, the particular features, structures or characteristics may be combined in any suitable manner, as would be apparent to one of ordinarily skill in the art from this disclosure, in one or more embodiments.

As used herein, unless otherwise specified, the use of ordinal adjectives "first," "second." "third." etc., to describe a common object, merely indicate that different instances of like objects are referred to, and are not intended to imply that the objects so described must be in a given sequence, either temporally, spatially, in ranking, or in any other manner.

In the claims below and the description herein, any one of the terms "comprising," "comprised of," or "which comprises" is an open term that means including at least the elements/features that follow, but not excluding others. Thus, the term "comprising," when used in the claims, should not be interpreted as being limitative to the means or elements or steps listed thereafter. For example, the scope of the expression "a device comprising A and B" should not be limited to devices consisting only of elements A and B.

Any one of the terms "including," or "which includes," or "that includes," as used herein, is also an open term that also means including at least the elements/features that follow the term, but not excluding others. Thus, "including" is synonymous with and means "comprising."

It should be appreciated that in the above description of exemplary embodiments of the invention, various features of the invention are sometimes grouped together in a single embodiment, figure, or description thereof, for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

Furthermore, while some embodiments described herein include some but not other features included in other embodiments, combining features of different embodiments would be understood by those skilled in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Thus, while there has been described what are believed to be the preferred embodiments of the invention, those skilled in the art will recognize that other and further modifications may be made thereto without departing from the spirit of the invention, and it is intended to claim all such changes and modifications as falling within the scope of the invention. For example, any formulas given above are merely representative of procedures that may be used. Functionality may be added or deleted from the block diagrams and operations may be interchanged among functional blocks. Steps may be added or deleted to methods described within the scope of the invention.

It will be appreciated by persons skilled in the art that numerous variations and/or modifications may be made to the disclosure as shown in the specific embodiments without departing from the scope of the disclosure as broadly described. The present embodiments are, therefore, to be considered in all respects as illustrative and not restrictive.

The invention claimed is:

1. A method of fabricating an electrical lead for a catheter, the method comprising:
    providing an elongate member having a proximal end and a distal end, and defining a lumen extending from the proximal end to the distal end, the elongate member comprising:
        a tubular member of non-conductive material,
        a braid of stainless steel wire applied over the tubular member, the braid configured to inhibit kinking of the elongate member,
        an intermediate layer of non-conductive material applied over the braid,
        a plurality of electrical conductors extending from the proximal end to the distal end laid on the intermediate layer, and
        an outer layer of non-conductive material applied over the plurality of electrical conductors to cover the plurality of electrical conductors; and
    accessing at least one of the plurality of electrical conductors and forming an electrode on an outer surface of the elongate member in electrical connection with the at least one of the electrical conductors, wherein the braid underlies the electrode.

2. The method of claim 1, further comprising arranging the plurality of electrical conductors helically on the intermediate layer about the tubular member.

3. The method of claim 1, further comprising inserting a tubular irrigation passage into the lumen of the elongate member.

4. The method of claim 3, wherein an irrigation fluid is supplied to the irrigation passage by an irrigation fluid connector element connected to a proximal end of a catheter handle.

5. The method of claim 3, wherein the irrigation passage is formed from a non-conductive material.

6. The method of claim 3, wherein the a cross-sectional shape of the irrigation passage is a kidney shape.

7. The method of claim 6, further comprising deforming the cross-sectional shape of the irrigation passage at its distal end into a circular shape by inserting an irrigation passage adapter to the distal end of the irrigation passage wherein the irrigation passage adapter abuts the distal end of the irrigation passage against an inner wall of the elongate member.

8. The method of claim 7, further comprising forming an end electrode by accessing at least one of the plurality of electrical conductors proximal the distal end of the elongate member and covering the distal end of the elongate member with an end electrode to overlie the at least one electrical conductor accessed and to be in electrical connection with the conductor.

9. The method of claim 8, further comprising forming a plurality of irrigation openings in the end electrode.

10. The method of claim 9, wherein the plurality of irrigation openings are arranged at circumferentially spaced intervals.

11. The method of claim 9, wherein a sealing aid is used to secure the irrigation passage adapter and the end electrode thereby to seal an irrigation fluid path from an irrigation fluid connector element through the irrigation passage and the irrigation openings.

12. An electrical lead for a catheter, the electrical lead comprising:
    an elongate member of non-conductive material having a proximal end and a distal end and defining a lumen extending from the proximal end to the distal end, the elongate member comprising:
        a tubular member of non-conductive material,
        a braid of stainless steel wire applied over the tubular member, the braid configured to inhibit kinking of the elongate member,
        an intermediate layer of non-conductive material applied over the braid,
        a plurality of electrical conductors extending from the proximal end to the distal end laid on the intermediate layer, and
        an outer layer of non-conductive material applied over the plurality of electrical conductors to cover the plurality of conductors; and
    at least one electrode on an outer surface of the elongate member in electrical communication with at least one of the plurality of electrical conductors through the outer layer, wherein the braid underlies the at least one electrode but is insulated from the at least one electrode by the intermediate non-conductive layer.

13. The electrical lead of claim 12, wherein the plurality of electrical conductors are arranged helically on the intermediate layer about the tubular member.

14. The electrical lead of claim 12, wherein a tubular irrigation passage is inserted into the lumen of the elongate member.

15. The electrical lead of claim 14, wherein an irrigation fluid is supplied to the irrigation passage by an irrigation fluid connector element connected to a proximal end of a catheter handle.

16. The electrical lead of claim 14, wherein the irrigation passage is formed from a non-conductive material.

17. The electrical lead of claim 14, wherein a cross-sectional shape of the irrigation passage is a kidney shape.

18. The electrical lead of claim 17, further comprising an irrigation passage adapter inserted into a lumen of the irrigation passage at its distal end, the irrigation passage adapter deforming the cross-sectional shape of the distal end of the irrigation passage into a circular cross-sectional shape, the irrigation passage adapter further abutting the distal end of the irrigation passage and pressing its circumference tightly against an inner wall of the elongate member.

19. The electrical lead of claim 18, further comprising an end electrode covering the distal end of the elongate member, the end electrode being in electrical communication with at least one of the plurality of electrical conductors through the outer layer.

20. The electrical lead of claim 19, wherein the end electrode comprises a plurality of irrigation openings.

21. The electrical lead of claim 20, wherein the plurality of irrigation openings are arranged at circumferentially spaced intervals.

22. The electrical lead of claim 20, wherein a sealing aid is used to secure the irrigation passage adapter and the end electrode thereby to seal an irrigation fluid path from an irrigation fluid connector element through the irrigation passage and the irrigation openings.

\* \* \* \* \*

UNITED STATES PATENT AND TRADEMARK OFFICE
CERTIFICATE OF CORRECTION

PATENT NO. : 10,849,684 B2
APPLICATION NO. : 14/894970
DATED : December 1, 2020
INVENTOR(S) : David Ogle, Roman Greifeneder and Warrick Heald It is certified that error appears in the above-identified patent and that said Letters Patent is hereby corrected as shown below:

On the Title Page
        In ITEM (54)    Line 1,    change "ELECTRICAL LEAD FOR" to
        --AN ELECTRICAL LEAD FOR--

In the Specification
        Column 6,    Line 20,    change "adjectives "first," "second." "third." etc.," to
        --adjectives "first," "second," "third," etc.,--

In the Claims
    Claim 6,    Column 7,    Line 53,    change "wherein the a cross-sectional" to
        --wherein a cross-sectional--

Signed and Sealed this
Fourth Day of May, 2021

Drew Hirshfeld
*Performing the Functions and Duties of the
Under Secretary of Commerce for Intellectual Property and
Director of the United States Patent and Trademark Office*